United States Patent
Gaudio

(10) Patent No.: US 10,702,710 B2
(45) Date of Patent: Jul. 7, 2020

(54) SYSTEM AND METHODS FOR PROCESSING IMAGES TO MEASURE COLLIMATOR LEAF AND COLLIMATOR PERFORMANCE

(71) Applicant: Varian Medical Systems, Inc., Palo Alto, CA (US)

(72) Inventor: Stephen Gaudio, Mountain View, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 0 days.

(21) Appl. No.: 15/722,815

(22) Filed: Oct. 2, 2017

(65) Prior Publication Data

US 2018/0085602 A1 Mar. 29, 2018

Related U.S. Application Data

(62) Division of application No. 15/299,837, filed on Oct. 21, 2016, now Pat. No. 9,776,018, which is a division of application No. 14/040,202, filed on Sep. 27, 2013, now Pat. No. 9,480,860.

(51) Int. Cl.
*A61N 5/10* (2006.01)

(52) U.S. Cl.
CPC ......... *A61N 5/1045* (2013.01); *A61N 5/1075* (2013.01); *A61N 5/1081* (2013.01); *A61N 2005/1095* (2013.01)

(58) Field of Classification Search
CPC .. A61N 5/1045; A61N 5/1048; A61N 5/1075; G21K 1/04; G21K 1/046
See application file for complete search history.

(56) References Cited

U.S. PATENT DOCUMENTS

| | | | |
|---|---|---|---|
| 6,382,796 B1 | 5/2002 | Ban | |
| 6,633,655 B1 | 10/2003 | Hong et al. | |
| 6,891,178 B2 * | 5/2005 | Xing | A61N 5/1075 250/397 |
| 6,891,179 B2 | 5/2005 | Xing | |
| 7,181,066 B1 | 2/2007 | Wagman et al. | |
| 8,280,003 B2 | 10/2012 | Torsti et al. | |
| 8,855,401 B2 | 10/2014 | Archie et al. | |
| 2005/0105830 A1 | 5/2005 | Chung et al. | |
| 2006/0072849 A1 | 4/2006 | Marc | |
| 2007/0086569 A1 | 4/2007 | Johnsen | |
| 2007/0092130 A1 | 4/2007 | Shishido et al. | |
| 2007/0164219 A1 | 7/2007 | Shishido et al. | |
| 2007/0201044 A1 | 8/2007 | Yamane | |
| 2008/0130982 A1 | 6/2008 | Kitamura et al. | |
| 2008/0298553 A1 | 12/2008 | Takahashi et al. | |
| 2008/0319311 A1 | 12/2008 | Hamadeh | |
| 2009/0214103 A1 | 8/2009 | Tanaka et al. | |
| 2009/0320554 A1 | 12/2009 | Watabe et al. | |
| 2010/0020931 A1 | 1/2010 | Otto et al. | |

(Continued)

*Primary Examiner* — Nicole M Ippolito
*Assistant Examiner* — Sean M Luck

(57) ABSTRACT

Systems and methods are proposed for accurate and efficient automatic measurement of jaw and leaf positioning in multi-leaf collimator imaging systems. Specifically, the method enables the automated and objective processing of images to determine characteristics of collimator jaws and MLC leaves. These novel techniques enable verification of collimator component positioning to ensure accurate beam modulation for radiation application procedures.

20 Claims, 9 Drawing Sheets

(56) References Cited

U.S. PATENT DOCUMENTS

| | | | |
|---|---|---|---|
| 2010/0031625 A1* | 2/2010 | Narayan | F01K 23/106 60/39.5 |
| 2010/0054538 A1 | 3/2010 | Boon | |
| 2010/0215147 A1 | 8/2010 | Muller et al. | |
| 2010/0232685 A1 | 9/2010 | Yokokawa et al. | |
| 2010/0316259 A1 | 12/2010 | Liu et al. | |
| 2011/0085643 A1 | 4/2011 | Zhu et al. | |
| 2011/0122423 A1 | 5/2011 | Jones et al. | |
| 2011/0135215 A1 | 6/2011 | Tay | |
| 2011/0199534 A1 | 8/2011 | Kawai | |
| 2011/0208477 A1 | 8/2011 | Hitomi et al. | |
| 2011/0228131 A1 | 9/2011 | Iwane | |
| 2011/0317924 A1 | 12/2011 | Fukushi et al. | |
| 2012/0012763 A1 | 1/2012 | Kuusela et al. | |
| 2012/0203490 A1 | 8/2012 | Sayeh et al. | |
| 2012/0232324 A1 | 9/2012 | Brusasco et al. | |

\* cited by examiner

Exemplary Computer System 900

SYSTEM AND METHODS FOR PROCESSING IMAGES TO MEASURE COLLIMATOR LEAF AND COLLIMATOR PERFORMANCE

CLAIM OF PRIORITY

This application claims the benefit from and is a divisional of U.S. patent application Ser. No. 14/040,202 by Stephen Gaudio, entitled "Systems and Methods for Processing Images to Measure Multi-Leaf Collimator, Collimator Jaw, and Collimator Performance," filed Sep. 27, 2013, which is incorporated herein by reference in its entirety.

TECHNICAL BACKGROUND

Radiation therapy (RT) is a popular and efficient method for cancer treatment, where ionizing radiation is used in an attempt to kill malignant tumor cells or to slow down their growth. RT is often combined with surgery, chemotherapy, or hormone therapy, but may also be used as a primary therapy mode. Radiation therapy may be administered as internal RT or brachytherapy or, more commonly, external beam RT.

Internal RT treatment typically includes placing one or more radioactive sources near a designated treatment area, either permanently or temporarily. Conversely, external beam RT typically involves directing radiation beams produced by sources located externally with respect to the patient or radiation subject to the afflicted treatment area. The beam can consist of photons, electrons, protons or other heavy ions; photons being (at present) the most commonly used particle type. Malignant cells are damaged by the ionizing radiation used during the RT. However, the damage from the radiation is not limited to malignant cells and thus, the dosage of radiation to healthy tissues outside the treatment volume is ideally minimized to avoid being similarly damaged.

The development of medical linear accelerators (linacs) have dramatically increased the practicality and efficiency of multi-field RT treatments. Even more recently, linacs have been equipped with specialized computer-controlled hardware devices, such as collimator jaws and multi-leaf collimators (MLCs). These devices have been developed to deliver fields conforming to the projection of the target with greater ease and accuracy. In more advanced applications, the collimator jaws and/or the individual leaves of an MLC are moved separately under computerized control systems at desired speeds during periods of radiation (e.g., beam-on). This has enabled the generation of spatially modulated radiation fields, since each leaf attenuates the beam for a different time period. The resulting intensity modulated radiotherapy (IMRT) has allowed the application of high dose volumes that conform more closely to the shape of complicated targets. The further integration of x-ray image receptors to the linac has enabled the imaging of the patient before each treatment session and the tracking of tumor motion during treatment delivery. These so-called image-guided RT methods have improved subject positioning accuracy, and have lead to techniques for restricting tumor motion during treatment.

However, while these developments allow programming of more accurate beam fields, the devices themselves are still subject to mechanical errors or measurement variances which may result in inaccuracies during radiation application. Traditionally, verification of the mechanical devices were performed by generating a sample image under certain pre-programmed conditions or with pre-defined parameters. The mechanical devices could be taken apart and measured, and the generated image would be manually measured to verify the positioning of the collimator components under these known conditions. However, such verification techniques can be extremely time and user intensive, require significant skill to perform, and are subject to user error.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

Systems and methods are proposed for accurate and efficient automatic measurement of static jaw and leaf positioning in multi-leaf collimator imaging systems. Specifically, the method enables the automatic processing of images to determine characteristics of collimator jaws and MLC leaves. These novel techniques enable verification of collimator component positioning to ensure accurate beam modulation for radiation therapy procedures.

According to an aspect, an image set acquired with a MLC system is processed to determine characteristics which may include, inter alia, characteristics such as an MLC general offset, center of rotation, and leaf edge and leaf end positions, MLC angle, and magnification factor. In an embodiment, individual leaves may be isolated by configuring the leaves in an alternating extension or "comb" pattern during image generation. An initial measurement of the leaf edge is performed based on input data (e.g., such as an image, expected MLC leaf positions, and expected collimator angle), and a local minimum and maximum are thereafter calculated. Pixel (luminance) values corresponding to the local minimum and maximum in the image are averaged and a position in the image corresponding to the averaged pixel value is thereafter derived and iteratively repeating the process until the resulting measure convergences sufficiently. The result is not restricted to integer values due to interpolation used in the algorithm. According to such an embodiment, systemic biases incurring from flatness and symmetry errors typical in megavolt beams are rendered negligible, and allows for the direct calculation of initial values instead of requiring pre-processing, that can be difficult and significantly more time-intensive.

According to another embodiment, measurement of the collimator jaws may also be performed according to a similar process, for an edge of the collimator jaw. As per the process for determining the leaf edges, an initial estimate of a jaw edge is performed based on input data (e.g., an image, expected jaw positions and expected collimator angle). Local minimum and maximum jaw edge positions are thereafter calculated and, once determined, luminance values corresponding to the pixels at the local minimum and maximum positions in the image are averaged, and used to determine the location of the average value similar to the process for the MLC.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Figure 1:
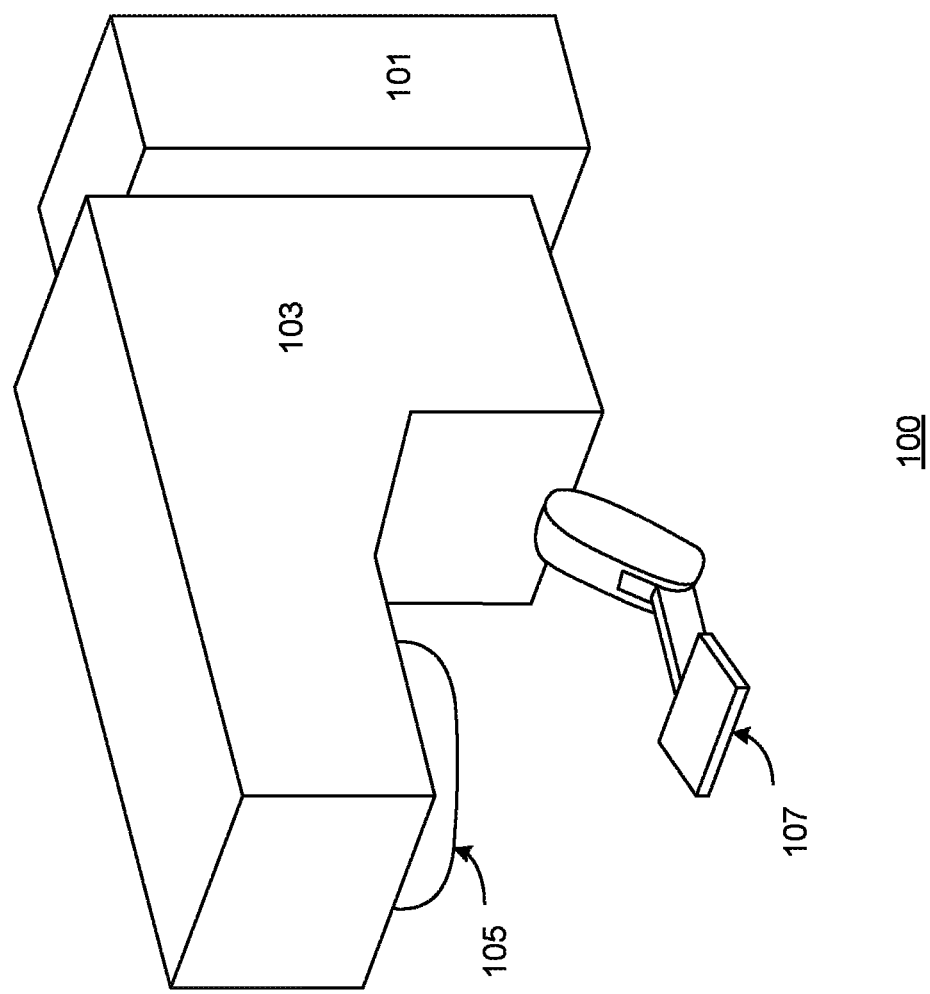
FIG. 1 depicts an illustration of an exemplary radiation therapy and imaging device, in accordance with embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in figures herein (e.g., FIGS. 5 and 7) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-usable medium, such as program modules, executed by one or more computers or other computing devices. Generally, program modules include routines, programs, objects, components, data structures, etc., that perform particular tasks or implement particular abstract data types. The functionality of the program modules may be combined or distributed as desired in various embodiments.

By way of example, and not limitation, computer-usable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information.

Communication media can embody computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer-readable media.

Exemplary Radiation Treatment and Imaging Machine

With reference now to FIG. 1, an illustration of an exemplary radiation therapy and imaging device 100 is depicted, in accordance with one embodiment. In one configuration, radiation therapy and imaging device 100 includes a support structure 101, a gantry 103, a treatment head 105 and an imager 107. In some embodiments, radiation therapy device 100 may include a communicatively coupled computing device for calculating dosages and processing images and/or a separate therapeutic radiation source for delivering radiation therapy.

In one embodiment, the end of gantry 103 is attached to the treatment head 105. The treatment head may include, or be coupled with a radiation source, such as a medial linear accelerator that generates radiation beams for therapy or imaging purposes. These generated radiation beams are delivered and/or modified by the treatment head. While receiving treatment or acquiring an image, a treatment or imaging subject is positioned (typically supine) below the radiation source 105 and between the source and the imager or detector 107. A target volume (generally disposed within or about the patient subject) is acquired. According to one embodiment, an image of the imaging subject is acquired by generating a volumetric image of the area within the subject. A volumetric image of the area is acquired by, for example, generating a three dimensional image using radiation source 105 in conjunction with the imager 107. According to an embodiment, the imaging device 100 may be used to generate imaging data with or without a subject. According to another embodiment, the imaging device may be used to generate imaging data according to a test pattern template while without a subject. The imaging data may consist of a single image or a plurality of images comprising an image set, each of which may be processed to automatically measure certain characteristics of the imaging system 100 to verify positioning of the collimator jaws and/or leaves of the multi-leaf collimator.

Exemplary Medical Linear Accelerator

Figure 2:
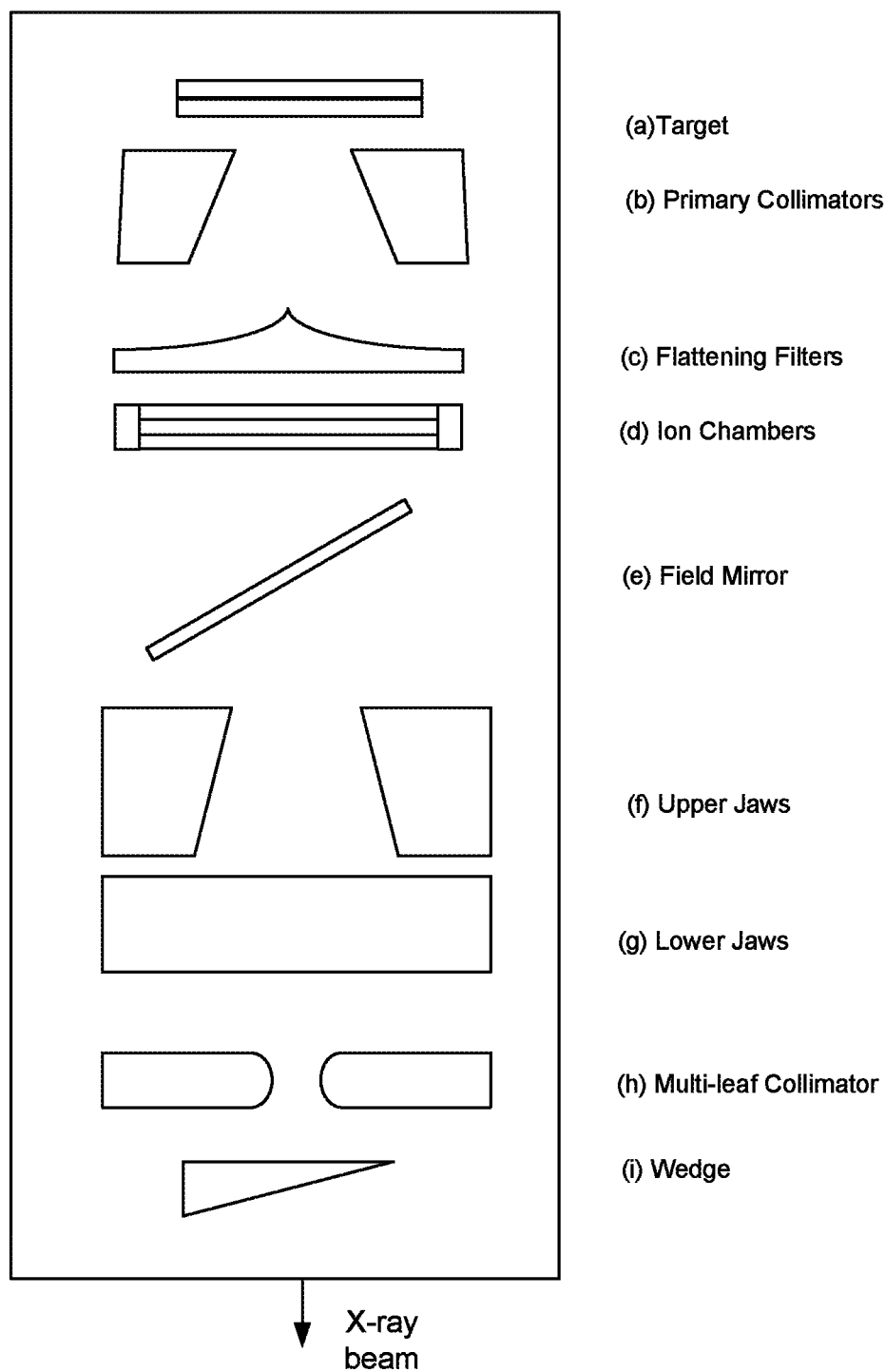
FIG. 2 depicts an illustration of an exemplary treatment head of a medical linear accelerator, in accordance with embodiments of the present invention.

With reference now to FIG. 2, an illustration of an exemplary treatment head 200 of a medical linear accelerator is depicted, in accordance with one embodiment. As presented, the treatment head 200 receives a primary electron beam, applied to a target (a) to generate photons that comprise the radiation treatment. The photons are further modified (attenuated, directed) by a plurality of components (b)-(i). In one configuration, after an accelerated primary electron beam emerges from a source (e.g., an electron gun), the electron beam will hit a target (a), commonly consisting of a high-Z metal, after which the electrons will produce what are referred to as "bremsstrahlung photons" (photon beam).

The primary photon beam is subsequently collimated initially by a primary collimator (b) and the photon fluence is differentially attenuated by a flattening filter (c) to produce a reasonably flat dose distribution. Next, a monitor ion chamber (d) and a field mirror (e) monitor the radiation by generating monitor units to correspond to detected primary photons passing through the monitor chamber (e.g., 97-100% of the signal, depending on field size) and back-scattered photons (e.g., the remaining 0-3% of the signal) of the primary photon beam when particles of the photon beam are intersected by the placement beam collimating and/or modulating devices (e.g., jaws, MLC leaves). Finally the photon beam is shaped and modulated by a collimating system (or sub-system) that may include various devices such as jaws (including an upper jaw (f) and a lower jaw (g), multi-leaf collimators (MLC) (h), and/or wedges and blocks (i), etc.

Multi-Leaf Collimator Configuration

Figure 3:
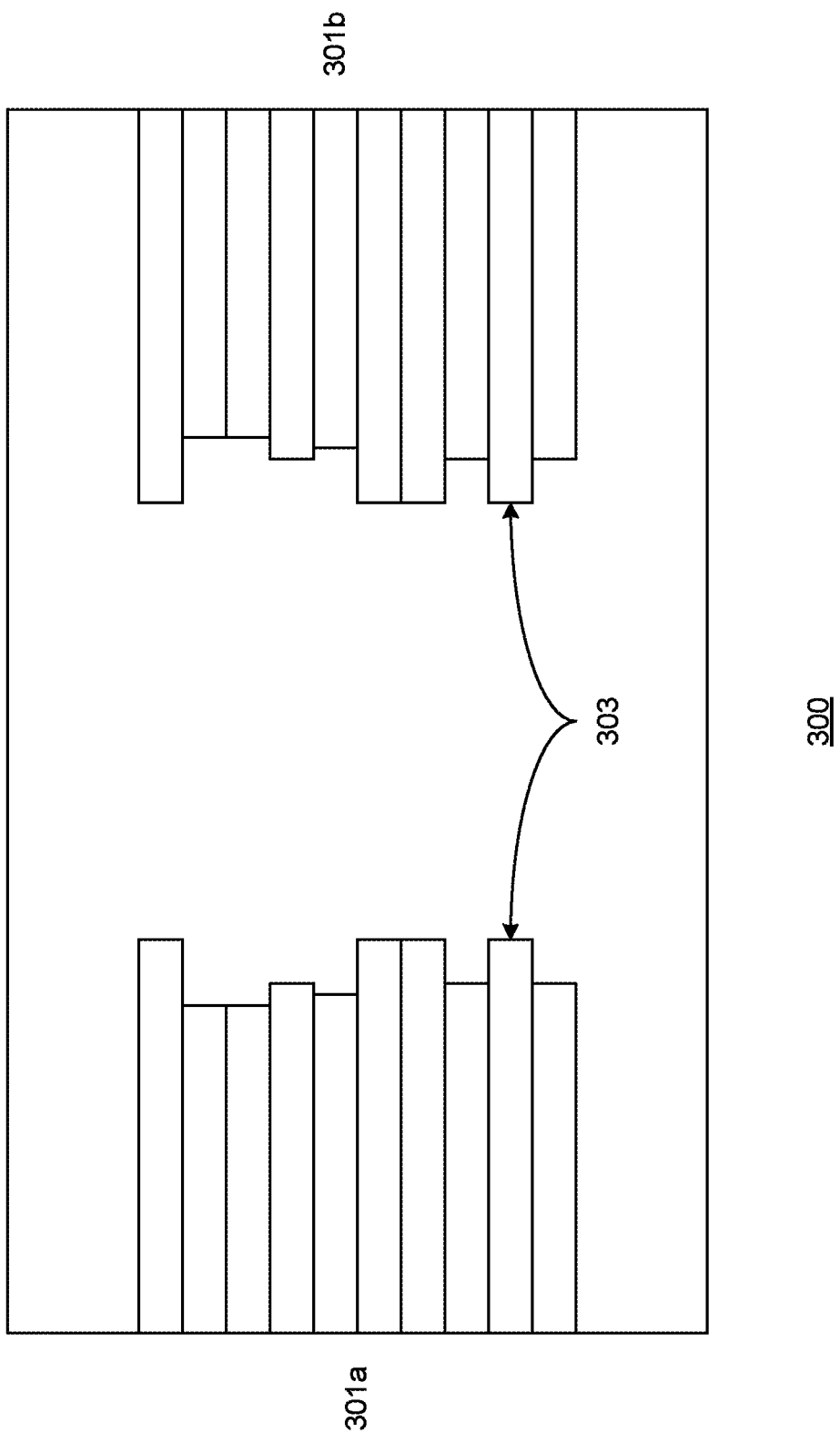
FIG. 3 depicts an illustration of an exemplary arrangement of a plurality of leaves of a multi-leaf collimator, in accordance with embodiments of the present invention.

FIG. 3 depicts an exemplary arrangement 300 of a plurality of leaves of a multi-leaf collimator, in accordance with one embodiment. As depicted in FIG. 3, a multi-leaf collimator may comprise one or more banks of leaves (e.g., left bank 301a, right bank 301b), each bank comprising a plurality of leaves 303. According to various embodiments, each of the leaves may be independently and variably extensible, and controlled by a motion control system comprised in, or coupled to, a radiation imaging device such as the device 100 described above with respect to FIG. 1.

Figure 4:
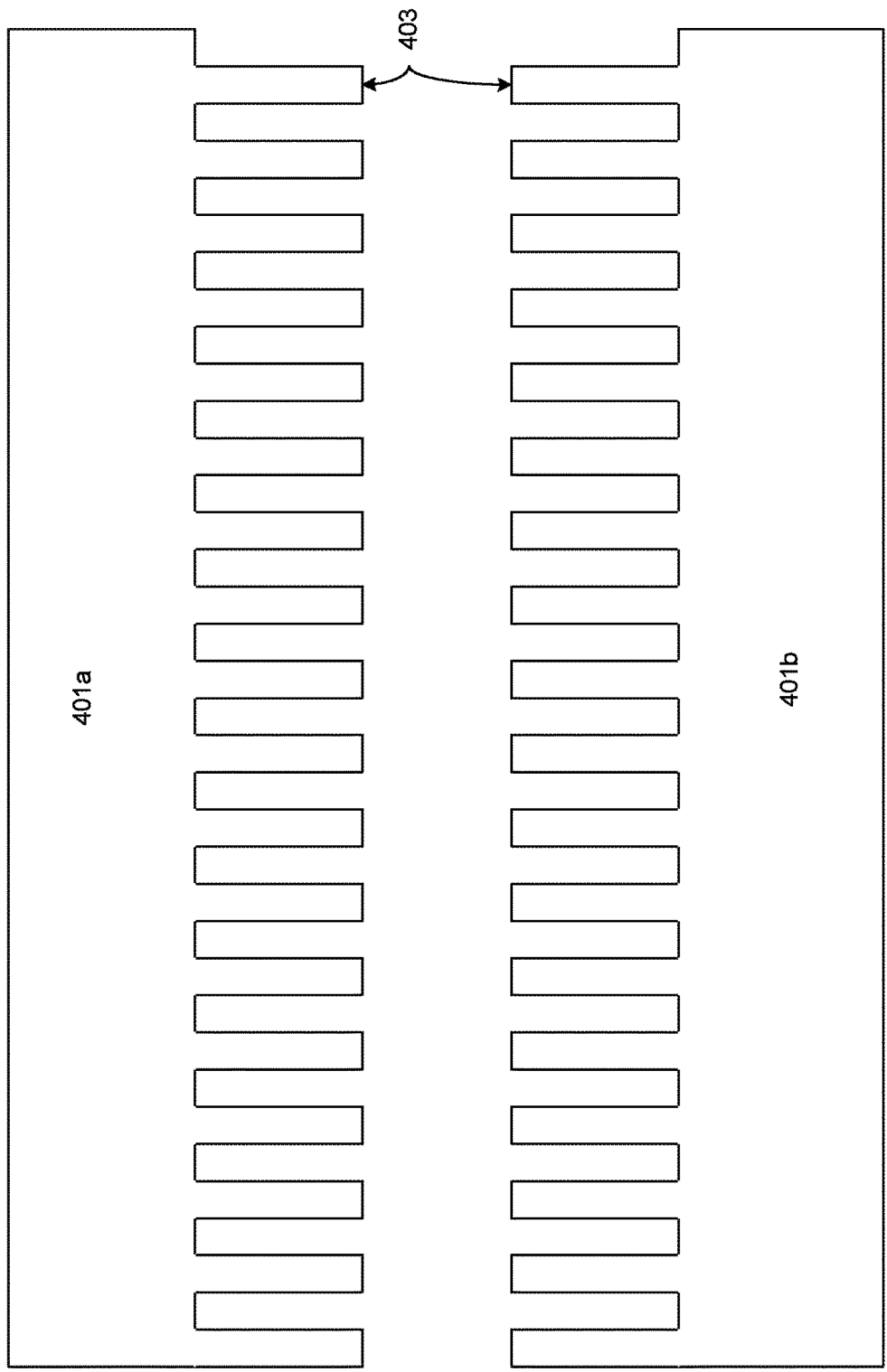
FIG. 4 depicts an illustration of an exemplary arrangement of a plurality of leaves of a multi-leaf collimator in an alternating extension configuration, in accordance with embodiments of the present invention.

FIG. 4 depicts an exemplary arrangement 400 of a plurality of leaves of a multi-leaf collimator system in an alternating extension configuration. According to an embodiment, measurements of the multi-leaf collimator may be performed by generating an image of the projection of the shadow cast by individual leaves. The individual leaves may be controlled via a control system to conform to a test pattern template, for example. Arrangement 400 depicts a configuration that allows measurement of a plurality of individual leaves. In an embodiment arrangement 400 depicts a plurality of banks of leaves (e.g., top bank 401a, bottom bank 401b), each comprising a plurality of leaves 403. According to one or more embodiments, not all leaves need to be available in the image for measurement since the algorithm will skip missing leaves without affecting the measurement of available leaves.

As depicted in FIG. 4, the leaves of each bank (401a, 401b) are arranged in an alternating extension or "comb" pattern, whereby alternating leaves are at least partially extended and retracted, such that each extended leave is immediately adjacent to a non-extended leaf on each side, and each non-extended leaf is immediately adjacent to an extended leaf on either side. According to these embodiments, multiple leaves can be independently and individually measured, and large panel imagers may be leveraged to include as many leaves as possible, thereby increasing an efficiency of the measurement process.

Exemplary Measurement of Leaves of a Multi-Leaf Collimator

Figure 5:
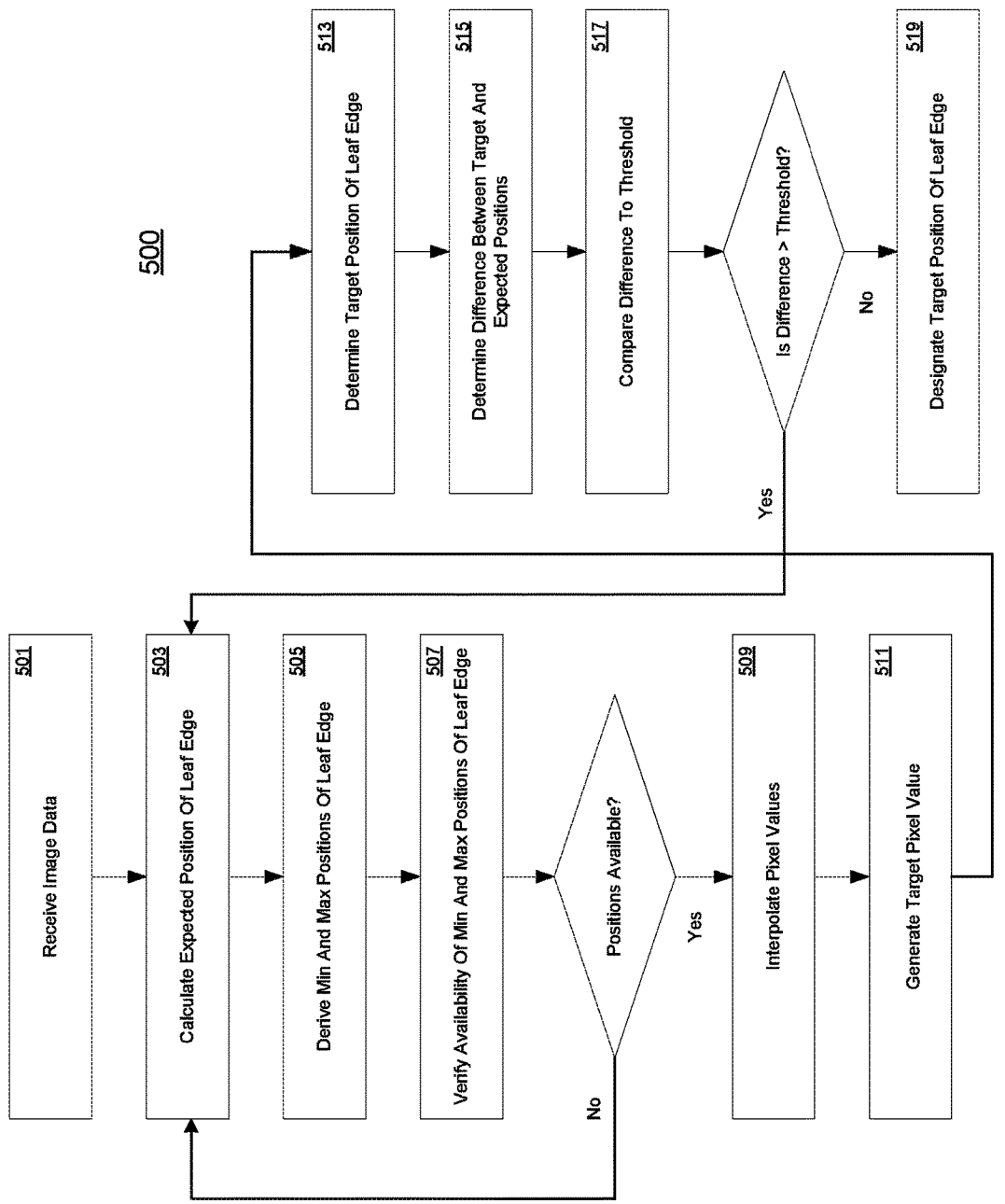
FIG. 5 depicts flowchart of a technique for measuring characteristics of a plurality of leaves in a multi-leaf collimator, in accordance with embodiments of the present invention.

FIG. 5 is a flowchart 500 of a technique for measuring characteristics of a plurality of leaves of a multi-leaf collimator based on an image, in accordance with one embodiment. This technique may be performed, for example, during image processing of one or more images generated by a radiation imaging device, such as imaging device 100 described above with respect to FIG. 1. Steps 501-519 describe exemplary steps comprising the process depicted in flowchart 500 in accordance with the various embodiments herein described. In one embodiment, the flowchart 500 is implemented as a portion of the computer-executable instructions and stored in a computer-readable medium. In one or more embodiments, the images generated by the imaging device for the purpose of leaf measurement are acquired by positioning the leaves in one or more positions according to a leaf test pattern. In one embodiment, the leaf positions may be set in accordance with one or more guidelines. These guidelines may include specific configurations, such as: alternating extensions separated by a minimal distance; and the separation of leaves of opposing banks by a minimal distance.

In one embodiment, flowchart 500 begins at step 501 upon the receipt of image data in an image processing device. The image data may be data generated by the imaging device, and may comprise one or more images of radiation collected in a radiation detector with the collimating system (or sub-system) operated to perform a test pattern template. The test pattern template may, according to some embodiments, position the leaves individually in a plurality of positions and/or orientations. Images generated by the imaging device in some instances may comprise a projection of the shadow cast by the leaves of the MLC from the radiation source, and captured by the detector. In still further embodiments, processing of the image may be performed in a computing device coupled to, or comprised within the image device.

According to a further embodiment, the imaging data may also include input corresponding to pre-entered characteristics of the imaging device. The input data may include, inter alia, but is not limited to data such as:

a. MLC image origin location: This may be expressed as a row-column coordinate pair, indicating a designated location of the origin in the image of a MLC coordinate frame, and corresponds to a pre-measured isocenter projection onto the detector panel as determined by previous testing;

b. MLC center of rotation: determined by image processing of a set of a plurality of images;

c. Estimated location of the isocenter of the image: based on the position of the detector panel;

d. Collimator angle: expressed as a single value per image. The collimator angle may be the reported collimator angle (as determined by an axis position sensor in the MLC) or the measured collimator angle as determined by MLC image processing;

e. Pixel Pitch: the scale factor between image pixels and centimeters in the isoplane as derived from the detector's vertical position, and expressed as a single value per image and calculated from the pre-determined native pixel height of the panel combined with a magnification factor (corresponding to the vertical position of the panel) or as determined by image processing;

f. Expected leaf widths: are expressed as a set of values corresponding to a design value for each leaf, and are precise widths defined by mechanical design, often fixed per MLC type; and g. Expected leaf end positions: are expressed as a set of values corresponding to planned leaf positions for each leaf for each leaf bank according to the particular test pattern template used.

At step 503, an expected position of a leaf edge in an image is calculated based on the image data received in step 501. The expected position may for example, be expressed as coordinates in a coordinate plane corresponding to the imager. At step 505, a local minimum position and a local maximum position are calculated based on the expected position determined in step 503. Each of the local minimum and maximum positions may be expressed as coordinates in the image plane. In an embodiment, the local minimum position and local maximum position are each calculated at a distance equivalent to half a leaf's width (received as input in step 501) away from the expected position. In further embodiments, each of the local minimum and local maximum positions is calculated in a pre-determined direction corresponding to the orientation of the MLC. For example, if a bank of leaves is oriented in a horizontal direction, the local minimum and local maximum positions are calculated along the X (horizontal) axis from the expected position.

At step 507, the availability of the local minimum and maximum positions calculated at step 505 is verified. Verification may be performed by, for example, comparing the coordinate values of the minimum and maximum positions with pre-determined limits of the imager and/or primary collimator. For example, a leaf expected to be at the very edge of the image may have a calculated minimum or maximum position that exceeds the framed area of the imager. If verified, the process proceeds to step 509. Otherwise, the process returns to step 503 to calculate a new expected position of the next leaf edge based on the input data.

At step 509, the pixel values of the image corresponding to the local minimum and maximum positions are interpolated. In one embodiment, the pixel values comprise the color values (in RGB color space) of the pixel at the coordinates of each of the local minimum and local maximum position. In alternate embodiments, the pixel values comprise the luminance value (e.g., in YUV space) at the coordinates of the local minimum and maximum position. A target pixel value is determined at step 511 based on the pixel values of the local minimum and maximum positions. In one embodiment, the target pixel value represents the likely position of a leaf edge, and may be calculated by averaging the pixel values of the local minimum and maximum positions.

At step 513, a target position corresponding to the target pixel value is calculated. In one or more embodiments, the target position is calculated by according to a bisection method. The bisection method may be performed, for example, by plotting the calculated values corresponding to the target, maximum, and minimum pixel values along a first axis; and the position values (along the direction of the line segment connecting the local minimum and maximum positions) of the expected, minimum, and maximum positions along the second axis in a graph. Bisecting the resulting line segment (or curve) and interpolating the bisected result generates the position (along the line segment) of the target position. Once calculated, the target position is compared to the expected position calculated at step 503, with the absolute (unsigned) difference being compared to a threshold value at step 517. If the difference is less than the threshold value, the target position is confirmed as the designated position of the leaf edge and the position is output.

However, if the difference is greater than the threshold value, steps 503-517 may be iteratively repeated until the difference is less than the threshold value to further refine the resultant output. Each iteration may use the target position determined at step 513 of the previous iteration to calculate the expected position calculated at step 503 in the following iteration. The target position determined by an iteration may be directly substituted as the expected position of the next iteration. In still further embodiments, once confirmed, the target position may be converted to length units at the isoplane by applying the pixel pitch (input as data) as a scale factor.

Figure 6:
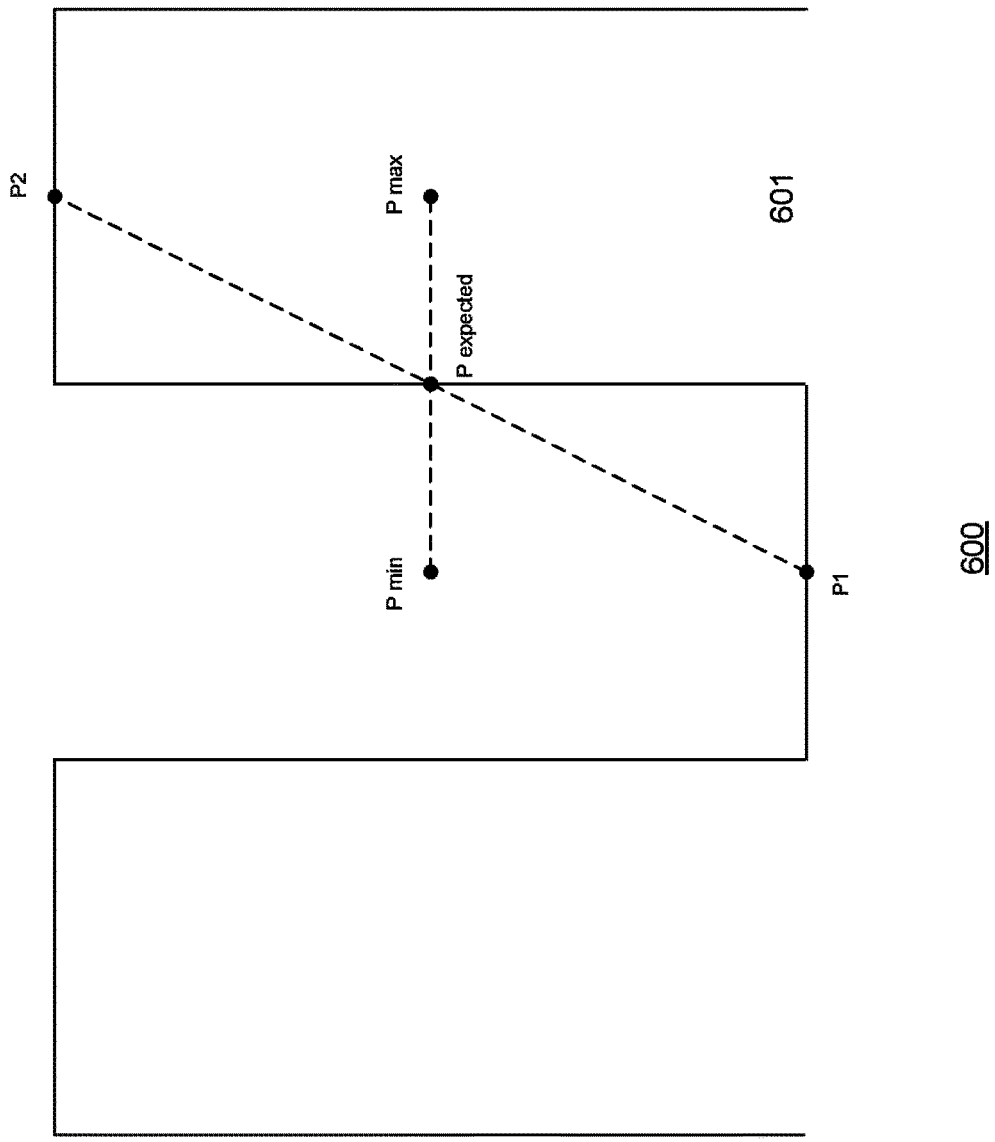
FIG. 6 depicts an illustration of exemplary measurements corresponding to individual leaves of a collimating system, in accordance with embodiments of the present invention.

FIG. 6 depicts an illustration 600 of exemplary measurements in an image generated with a multi-leaf collimator, in accordance with embodiments of the present invention. In an embodiment, FIG. 6 depicts measurements performed on an individual leaf (601) at the beginning of a third iteration of the process performed in flowchart 500. As shown in FIG. 6, two previous iterations of the process described in flowchart 500 were performed, resulting in two "target positions" (P1, P2). In one or more embodiments, if the distance from P1 and P2 is greater than a pre-determined threshold, the target position may be used to calculate the initial guess value for the expected position (in step 503) in a subsequent iteration of the process. With respect to FIG. 6, the expected position is derived by taking the average value of the previous two iterations (P1, P2). According to the next step in the process depicted in FIG. 5, local minimum and maximum positions (P min, P max) are calculated at a leafs width apart along an axis (as depicted, the horizontal or X-axis), with the expected position (P expected) at the midpoint of a line segment connecting the minimum and maximum position. Once the expected position and local minimum and maximum positions have been determined (steps 503 and 505), the remaining steps in the process may be performed to derive the next target position until the leaf end/side edge in an image has been confirmed. In an embodiment, once a target position is confirmed, a leaf centerline and a leaf end position may be determined by referencing the input data corresponding to the MLC. The leaf centerline for a leaf corresponds to the bisecting line along the direction of extension, and the leaf end position corresponds to the measured position (x) component of the location of a single leaf end.

Several associated advantages are possible through the application of the above described method to successively approximate the location of a leaf end/side edge in an image. These advantages include rendering systematic bias incurred from flatness and symmetry errors (inherent in radiation beams) negligible, and providing insensitivity to initial guess values, which allows for direct calculation of initial guess values instead of requiring substantial and/or costly image pre-processing.

According to still further embodiments, once a leaf side edge is determined, the location of the other leaf side edge for the same leaf may be derived (based on the pre-specified leaf width). This calculation may be performed for one or more leaves in the image. Subsequently, the leaf centerline offsets for each leaf can be measured by averaging the locations of both side edges of the leaf. The leaf centerline offset measurements correspond to the measured offset (Y)

component of the location of a single leaf centerline and are independent of measured leaf end position errors, which arise from leaf actuation error, which itself can involve servo error, manufacturing variation, calibration errors, etc. Once determined, the measured leaf centerline offset is then compared to the expected leaf centerline offset to determine the centerline error. In one or more embodiments, the expected leaf centerline offset is determined from the design of the multi-leaf collimator and the MLC image origin. The measured centerline offset error is used for subsequent analysis as described below.

In one or more embodiments, the leaf centerline offset error measurements can be used to determine collimator angle, pixel pitch, and an MLC general offset for an image. For each available nth centerline, a rotation error can be calculated according to:

$$\text{Theta}_n = \arctan(X_n - Y_n)$$

Where $X_n$ is the expected centerline offset, $Y_n$ is the measured centerline offset, and $\text{Theta}_n$ is the angle formed between the expected and measured centerline offsets. A collimator angle error may be subsequently calculated by averaging the Theta values corresponding to the leafs in the image. The collimator angle value provided as input at step 501 of FIG. 5 can be thereafter updated by adding the previous collimator value with the derived collimator angle error. Once the updated collimator angle is determined, the image can be reprocessed with the updated collimator angle to define a coordinate frame for the multi-leaf collimator. According to an aspect, the coordinate frame may be expressed as an XY Cartesian coordinate system which serves as the basis for location measures, and may be defined by either assumed or measured values for the origin location, orientation, and scale.

In one or more embodiments, for each bank of leaves of the multi-leaf collimator, a linear relation can be calculated between expected leaf centerline offsets and measured leaf centerline offsets. In further embodiments, the linear relation may be a best fit linear relation and be expressed in slope-intercept form. Thereafter, a general offset error can be calculated as the average of the intercepts of the linear relation (best fit lines). The general offset represents the measured signed distance between the MLC offset centerline and the MLC image origin. In yet further embodiments, the general offset error may be calculated as the weighted average of the intercepts, weighted according to the number of leaves measured in each bank of leaves.

In one or more embodiments, with the general offset error calculated, the MLC general offset can be updated by summing the previous MLC general offset (related to the MLC origin provided as input and as determined during a factory alignment process) with the general offset error. The linear relation calculated between expected leaf centerline offsets and measured leaf centerline offsets can also be used to calculate magnification factor errors, by taking the weighted average of the intercepts of the relation (best fit lines) for each bank, weighted according to the number of leaves measured in each bank. The pixel pitch provided as input is thereafter updated to include the magnification factor error as an updated pixel pitch. Once the updated MLC general offset and pixel pitch have been determined, the image is reprocessed using the updated parameters to further define the coordinate frame. In further embodiments, calculation of the collimator angle error, the MLC general offset error, and the magnification factor error can be compared to one or more threshold values and iteratively repeated until the errors are less than the threshold values or lie within an acceptable range.

By redefining the collimator angle, pixel pitch, and MLC general offset, further measurements become immune to errors of the leaf end position, which may be beset with a wide variety of errors that would otherwise be difficult to decouple from the original, provided collimator angle, pixel pitch, and MLC general offset values.

According to another aspect of the claimed subject matter, measurements may be performed for an entire image set comprising a plurality of images. For example, the measurements described above may be performed for one or more images of the image set to generate a corresponding set of MLC general offset measures, which can then be leveraged to determine the location of an MLC center of rotation and other errors such as MLC offset eccentricity and MLC offset runout.

The location of the MLC center of rotation corresponds to the measured point of revolution of the MLC image and can be determined by constructing a best fit circle within the set of MLC general offsets. The MLC offset eccentricity corresponds to the average of measured MLC general offsets for an MLC image set and can be calculated by averaging the value for the per-image MLC offsets. The MLC offset runout corresponds to the variation of measured MLC general offsets for an MLC image set. Measurement of the MLC center of rotation, eccentricity, runout, along with the positions of the leaf ends, leaf sides, and leaf centerlines as described above provides several advantages over traditional measurement techniques. For example, measurement of the MLC offset eccentricity aids in the assessment of misalignment between the MLC and collimator bearing axis. Meanwhile, the variation in the MLC center of rotation in the imager as the gantry rotates helps to indicate stability and quality of the MLC assembly and the imager/detector panel positioning system. Measurement of the runout provides a measure of collimator bearing performance, while the measurement of the leaf end, side, and centerline positions with respect to the MLC center of rotation can provide insight into MLC accuracy, independent of isocenter error, and can provide a robust method of assessing the collimator system or subsystem performance for the purpose of validation.

Exemplary Measurement of Collimator Jaws

Figure 7:
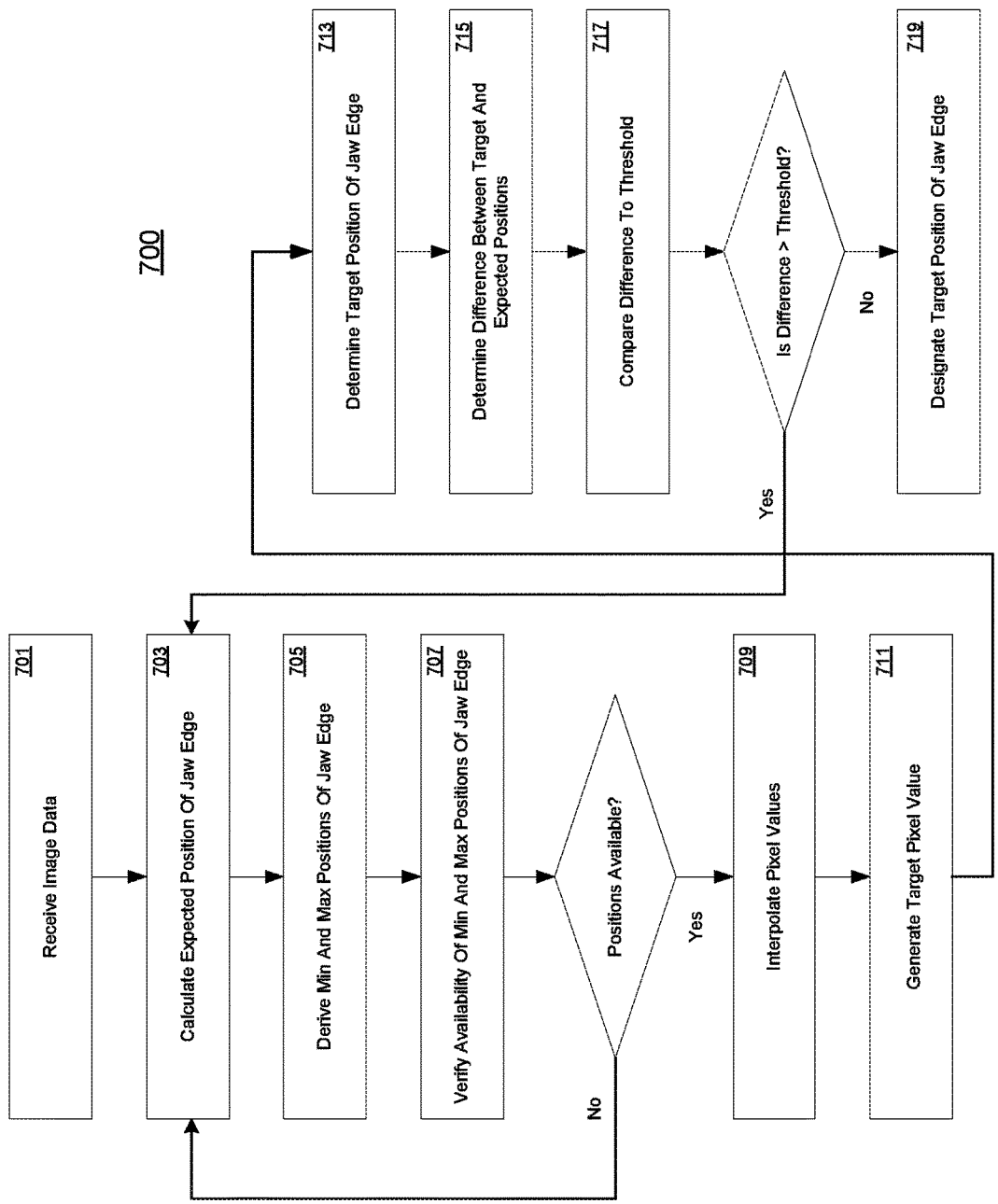
FIG. 7 depicts a flowchart of a technique for measuring characteristics of a set of collimator jaws in a multi-leaf collimator, in accordance with embodiments of the present invention.

FIG. 7 is a flowchart 700 of a technique for measuring characteristics of a plurality of collimator jaws of a collimating system based on an image, in accordance with one embodiment. This technique may be performed, for example, during image processing of one or more images generated by a radiation imaging device, such as imaging device 100 described above with respect to FIG. 1. Steps 701-719 describe exemplary steps comprising the process depicted in flowchart 700 in accordance with the various embodiments herein described. In one embodiment, the flowchart 700 is implemented as a portion of the computer-executable instructions and stored in a computer-readable medium. In one or more embodiments, the images generated by the imaging device for the purpose of jaw measurement are acquired by positioning the jaws in one or more positions according to a jaw test pattern. In one embodiment, the jaw positions are set to maximize the length of jaw edge visible in the image for one or more (or all) possible collimator angles. Alternate jaws positions may be employed which enable a measure of performance across the operational range of each jaw.

In one or more embodiments, processing of the jaw image(s) applies similar concepts—such as linear interpolation—as the processing of the MLC image(s). Likewise, jaw image processing begins with edge detection, similar to the process depicted in flowchart 500 with respect to leaf edge detection. In one embodiment, flowchart 700 begins at step 701 upon the receipt of image data in an image processing device. The image data may be data generated by the imaging device, and may comprise one or more images of radiation collected in a radiation detector with the collimating system (or sub-system) operated to perform a test pattern template. The test pattern template may, according to some embodiments, position the jaws in a plurality of positions and/or orientations. Images generated by the imaging device in some instances may comprise a projection of the shadow cast by collimating jaws of the collimator system or sub-system from the radiation source, and captured by the detector. In still further embodiments, processing of the image may be performed in a computing device coupled to, or comprised within the image device.

According to a further embodiment, the imaging data may also include input corresponding to pre-entered characteristics of the imaging device. The input data may include, inter alia, but is not limited to data such as:
 a. Jaw image origin location. This may be expressed as a row-column coordinate pair, indicating a designated location of the origin in the image of a Jaw coordinate frame, and corresponds to a pre-measured isocenter projection onto the detector panel as determined by previous testing;
 b. Jaw center of rotation determined by image processing;
 c. Estimated location of the isocenter of the image, based on the position of the detector panel;
 d. Collimator angle, expressed as a single value per image. The collimator angle may be the reported collimator angle (as determined by axis position sensors) or the measured collimator angle as determined by image processing;
 e. Pixel Pitch, the scale factor between image pixels and centimeters in the isoplane as derived from the detector's vertical position, and expressed as a single value per image and calculated from the pre-determined native pixel height of the panel combined with a magnification factor (corresponding to the vertical position of the panel) or as determined by image processing;
 f. Expected jaw positions are reported by the jaw position sensor; and
 g. User specified values that may include values for sample spacing, sample corner margin, and sample radius, which are parameters to control the geometry of sample zones.

At step 703, an expected position of a jaw edge in an image is calculated based on the image data received in step 701. The expected position may for example, be expressed as coordinates in a coordinate plane corresponding to the imager. At step 705, a local minimum position and a local maximum position corresponding to the expected position are calculated based on the expected position determined in step 703. Each of the local minimum and maximum positions may be expressed as coordinates in the image plane. At step 707, the availability of the local minimum and maximum positions calculated at step 705 is verified. Verification may be performed by, for example, comparing the coordinate values of the minimum and maximum positions with pre-determined limits of the imager and/or primary collimator. For example, a jaw expected to be at the very edge of the image may have a calculated minimum or maximum position that exceeds the framed area of the imager. If verified, the process proceeds to step 709. Otherwise, the process returns to step 703 to calculate a new expected position of a jaw edge based on the input data.

At step 709, the pixel values of the image corresponding to the local minimum and maximum positions are interpolated. In one embodiment, the pixel values comprise the color values (in RGB color space) of the pixel at the coordinates of each of the local minimum and local maximum position. In alternate embodiments, the pixel values comprise the luminance value (e.g., in YUV space) at the coordinates of the local minimum and maximum position. A target pixel value is determined at step 711 based on the pixel values of the local minimum and maximum positions. In one embodiment, the target pixel value represents the likely position of a jaw edge, and may be calculated by averaging the pixel values of the local minimum and maximum positions.

At step 713, a target position corresponding to the target pixel value is calculated. In one or more embodiments, the target position is calculated by according to a bisection method. The bisection method may be performed, for example, by plotting the calculated values corresponding to the target, maximum, and minimum pixel values along a first axis; and the position values (along a horizontal orientation, for example) of the expected, minimum, and maximum positions along the second axis in a graph. Bisecting the resulting line segment (or curve) and interpolating the bisected result generates the position (in the horizontal orientation) of the target position. Once calculated, the target position is compared to the expected position calculated at step 703, with the absolute (unsigned) difference being compared to a threshold value at step 717. If the difference is less than the threshold value, the target position is confirmed as the designated position of the jaw edge and the position is output.

However, if the difference is greater than the threshold value, steps 703-717 may be iteratively repeated until the difference is less than the threshold value to further refine the resultant output. Each subsequent iteration may use the target position determined at step 713 of the previous iteration to calculate the expected position calculated at step 703 in the following iteration. The target position determined by an iteration may be directly substituted as the expected position of the next iteration. In still further embodiments, once confirmed, the target position may be converted to length units at the isoplane by applying the pixel pitch (input as data) as a scale factor.

Figure 8:
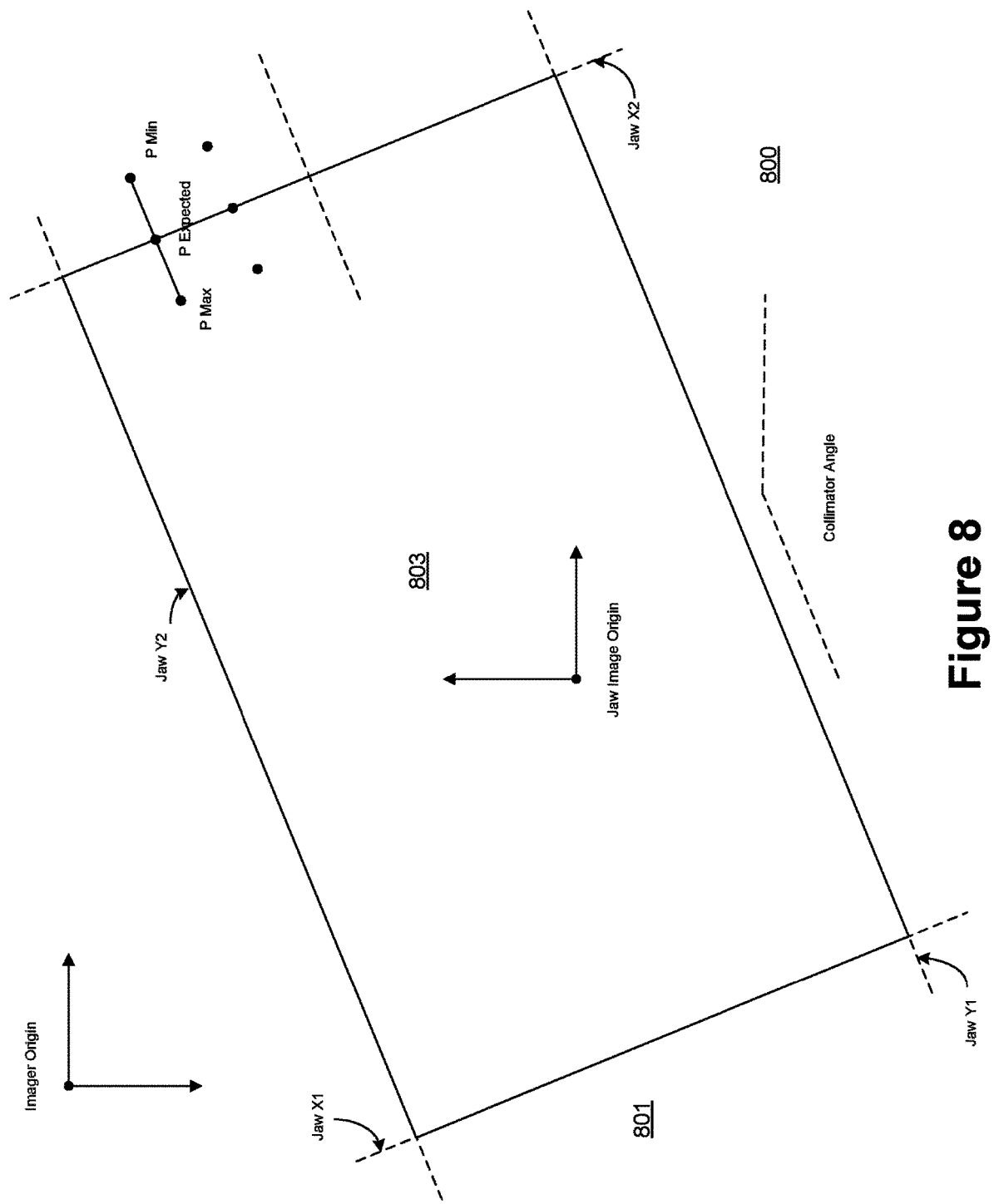
FIG. 8 depicts an illustration of exemplary measurements corresponding to collimator jaws of a collimating system, in accordance with embodiments of the present invention, in accordance with embodiments of the present invention.

FIG. 8 depicts an illustration 800 of exemplary measurements in an image generated with collimator jaws, in accordance with embodiments of the present invention. In an embodiment, FIG. 8 depicts measurements performed on a jaw during an iteration of the process performed in flowchart 800. FIG. 8 depicts a plurality of jaws 801 (e.g., jaws X1, X2, Y1, Y2) establishing a border around an image plane 803, as defined by the imager origin, jaw image origin, and collimator angle (each provided as input in step 701, for example). During an iteration of the process, a set of initial estimated positions is determined (P expected), and local maximum and minimum positions are calculated based on the estimated position, and the user specified value of sample radius. Once the expected position and local minimum and maximum positions have been determined (steps 703 and 705), the remaining steps in the process may be performed to derive the next target position until the jaw edge in an image has been confirmed.

In one or more embodiments, a plurality of images may be acquired by the imaging system and collected as a jaw image set. Performing the process described above with respect to FIG. 7 for some or all of the images yields a corresponding set of jaw position measures, which can be used to determine the location of a jaw center of rotation and the associated jaw runout error per jaw.

The jaw center of rotation can be calculated as the center of a circle constructed from a set of best fit lines, similar to how the center of rotation for the MLC is constructed from MLC offset centerlines. The location of the jaw center of rotation (per jaw) can be calculated as a function of the gantry angle, received as input and/or pre-determined as part of the test pattern template. Per jaw, the measured jaw positions can be used to calculate the jaw runout, which represents the absolute difference between the maximum and minimum jaw position values. Jaw runout is the sum of both mechanical error (collimator bearing runout, for example) and runtime servo error (e.g., stead state error). Once determined, the jaw image set may be reprocessed using the jaw center of rotation as the jaw image origin to generate measures of jaw positions.

Measurement of the jaw center of rotation, magnitude of the jaw runout, along with the positions of the jaws as described above provides additional advantages over traditional image processing techniques. For example, variation in the jaw center of rotation indicates stability and quality of the jaw and the imager/detector panel positioning system. Measurement of the jaw runout provides a measure of the combined effect of mechanical runout and jaw servo error, and the measure of the jaw position with respect to the jaw center of rotation provides insight into jaw accuracy, independent of isocenter error, and can provide another effective method of assessing the collimator system or subsystem performance for the purpose of validation.

Exemplary Computing Device

Figure 9:
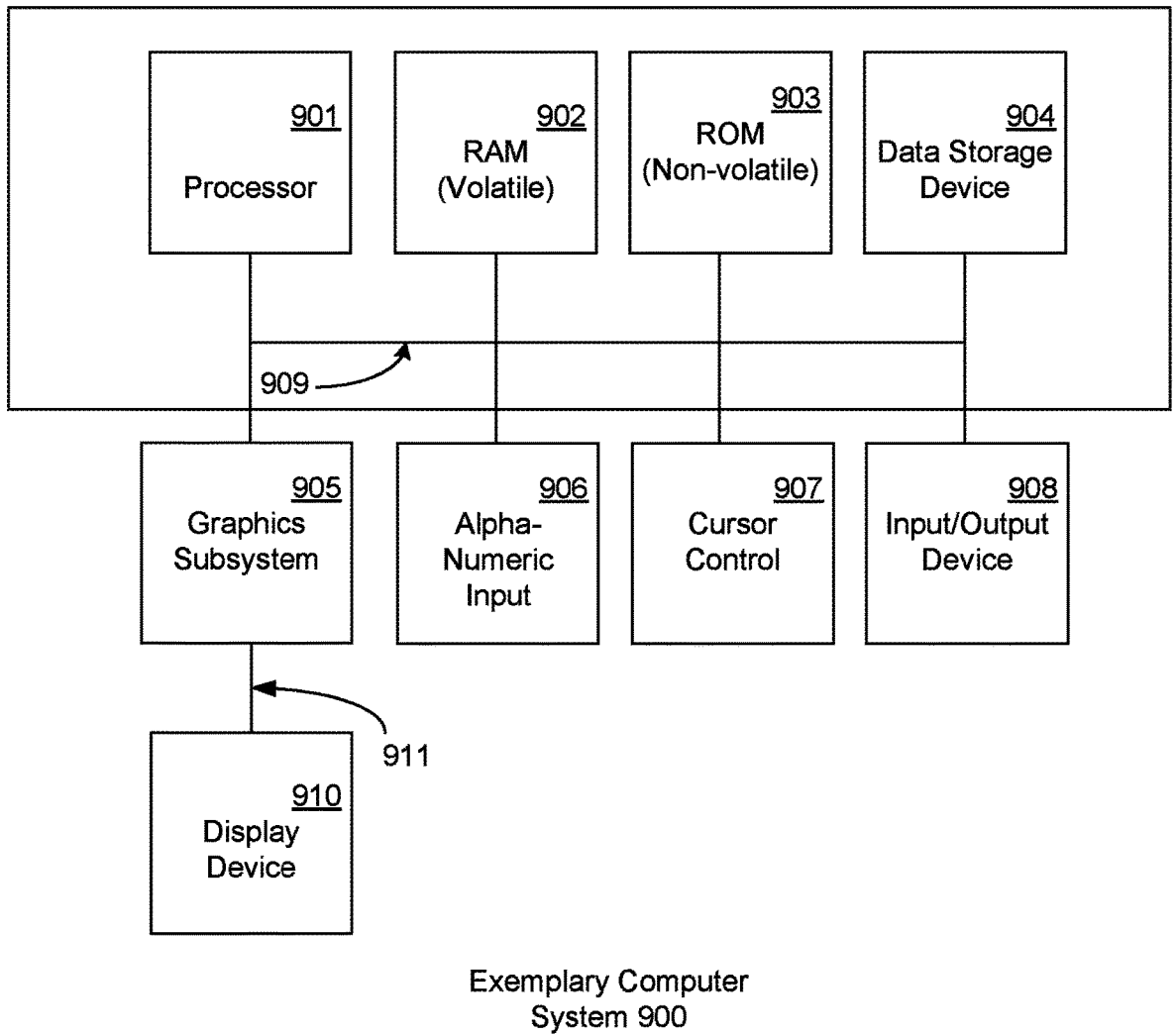
FIG. 9 depicts an exemplary computing environment, in accordance with embodiments of the present invention.

As presented in FIG. 9, an exemplary system upon which embodiments of the present invention may be implemented includes a general purpose computing system environment, such as computing system 900. For example, the image processing device in which processing of images generated through the imaging device (100) may, in one or more embodiments, be implemented in a computing environment, such as computing system 900. In its most basic configuration, computing system 900 typically includes at least one processing unit 901 and memory, and an address/data bus 909 (or other interface) for communicating information. Depending on the exact configuration and type of computing system environment, memory may be volatile (such as RAM 902), non-volatile (such as ROM 903, flash memory, etc.) or some combination of the two.

Computer system 900 may also comprise an optional graphics subsystem 905 for presenting information to the computer user, e.g., by displaying information on an attached display device 910, connected by a video cable 911. According to embodiments of the present claimed invention, the graphics subsystem 905 may be coupled directly to the display device 910 through the video cable 911. A graphical user interface of an application for controlling a medical linear accelerator executing in the computer system 900 may be generated in the graphics subsystem 905, for example, and displayed to the user in the display device 910. In alternate embodiments, display device 910 may be integrated into the computing system (e.g., a laptop or netbook display panel) and will not require a video cable 911. In one embodiment, the processes 500 and 700 may be performed, in whole or in part, by graphics subsystem 905 in conjunction with the processor 901 and memory 902, with any resulting output displayed in attached display device 910.

Additionally, computing system 900 may also have additional features/functionality. For example, computing system 900 may also include additional storage (removable and/or non-removable) including, but not limited to, magnetic or optical disks or tape. Such additional storage is illustrated in FIG. 9 by data storage device 907. Computer storage media includes volatile and nonvolatile, removable and non-removable media implemented in any method or technology for storage of information such as computer readable instructions, data structures, program modules or other data. RAM 902, ROM 903, and data storage device 907 are all examples of computer storage media.

Computer system 900 also comprises an optional alphanumeric input device 906, an optional cursor control or directing device 907, and one or more signal communication interfaces (input/output devices, e.g., a network interface card) 909. Optional alphanumeric input device 906 can communicate information and command selections to central processor 901. Optional cursor control or directing device 907 is coupled to bus 909 for communicating user input information and command selections to central processor 901. Signal communication interface (input/output device) 909, also coupled to bus 909, can be a serial port. Communication interface 909 may also include wireless communication mechanisms. Using communication interface 909, computer system 900 can be communicatively coupled to other computer systems over a communication network such as the Internet or an intranet (e.g., a local area network), or can receive data (e.g., a digital television signal).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A radiation system comprising:
   a gantry;
   a radiation source coupled to the gantry and operable to generate a stream of irradiated particles;
   a multi-leaf collimator (MLC) comprising a plurality of leaves configured to attenuate the stream of irradiated particles;
   a detector coupled to the gantry and operable to receive the stream of irradiated particles; and
   an image processor coupled to the detector and operable to generate image data corresponding to an image from the stream of irradiated particles received in the detector, wherein the image processor is further configured to calculate a plurality of measurements corresponding to a plurality of respective leaf positions of the plurality of leaves based on the image generated by the image processor and pre-entered characteristics corresponding to the radiation system and the image data, the pre-entered characteristics comprising a plurality of first predetermined characteristics related to the MLC and a plurality of second predetermined characteristics related to the detector or the image processor.

2. The radiation system of claim 1, wherein the image comprises the plurality of leaves in an alternating extension arrangement.

3. The radiation system of claim 1, wherein the image comprises a first image of a set of images.

4. The radiation system of claim 3, wherein the plurality of measurements are related to the first image and comprise at least one of a static relative location of a leaf end of a first leaf of the plurality of leaves, a static relative location of a plurality of leaf sides corresponding to the first leaf of the plurality of leaves, a static relative angle of the MLC, and a static pixel pitch at an isoplane corresponding to the detector.

5. The radiation system of claim 4, further comprising an axis position sensor configured to measure an angle value of the MLC.

6. The radiation system of claim 5, wherein the static relative angle of the MLC is measured based on the angle value from the axis position sensor.

7. The radiation system of claim 3, wherein the plurality of measurements are related to the set of images, and comprise at least one of a center of rotation corresponding to the MLC, an offset eccentricity corresponding to the MLC, and an offset runout corresponding to the MLC.

8. The radiation system of claim 1, wherein the image comprises a two dimensional matrix corresponding to a panel size of the detector.

9. A radiation therapy and imaging system comprising:
a source of a radiation beam;
a multi-leaf collimator (MLC) operable to modify the radiation beam; and
a radiation imager operable to receive and detect radiation from the radiation beam to generate an image that shows the MLC, wherein the radiation therapy and imaging system is further operable to access pre-entered characteristics corresponding to the radiation therapy and imaging system and the image, the pre-entered characteristics comprising a plurality of first predetermined characteristics related to the MLC and a plurality of second predetermined characteristics related to the radiation imager, and wherein the radiation therapy and imaging system is further operable to use the pre-entered characteristics and the image to verify a position of the MLC by iteratively converging a calculated position, which is based on a plurality of pixel values of the image, relative to an expected position.

10. The radiation therapy and imaging system of claim 9, further operable to use the image to determine a plurality of additional characteristics related to the MLC.

11. The radiation therapy and imaging system of claim 10, further operable to use at least one of the additional characteristics to update at least one of the first predetermined characteristics.

12. The radiation therapy and imaging system of claim 10, further operable to use at least one of the additional characteristics to update at least one of the second predetermined characteristics.

13. The radiation therapy and imaging system of claim 10, further operable to use the additional characteristics to update the position of the MLC.

14. The radiation therapy and imaging system of claim 10, further operable to use at least one of the additional characteristics to assess alignment, stability, performance, or accuracy of the MLC.

15. A radiation therapy and imaging system comprising:
a radiation source that is configured to generate a radiation beam;
a multi-leaf collimator (MLC) operable to modify the radiation beam and comprising a plurality of leaves; and
a radiation imager operable to receive and detect radiation from the radiation beam to generate an image that shows the plurality of leaves, wherein the radiation therapy and imaging system is further operable to access pre-entered characteristics corresponding to the radiation therapy and imaging system and the image, the pre-entered characteristics comprising a plurality of first predetermined characteristics related to the MLC and a plurality of second predetermined characteristics related to the radiation imager, and wherein the radiation therapy and imaging system is further operable to use the pre-entered characteristics and the image to verify a plurality of respective leaf positions of the plurality of leaves by iteratively converging a plurality of respective calculated leaf positions, which are based on a plurality of pixel values of the image, relative to a plurality of respective expected leaf positions.

16. The radiation therapy and imaging system of claim 15, further operable to use the image to determine a plurality of additional characteristics related to the MLC.

17. The radiation therapy and imaging system of claim 16, further operable to use at least one of the additional characteristics to update at least one of the first predetermined characteristics.

18. The radiation therapy and imaging system of claim 16, further operable to use at least one of the additional characteristics to update at least one of the second predetermined characteristics.

19. The radiation therapy and imaging system of claim 16, further operable to use the additional characteristics to update the plurality of respective leaf positions of the plurality of leaves.

20. The radiation therapy and imaging system of claim 16, further operable to use at least one of the additional characteristics to assess alignment, stability, performance, or accuracy of the MLC.

* * * * *